United States Patent [19]
Gelfand et al.

[11] Patent Number: 5,939,292
[45] Date of Patent: Aug. 17, 1999

[54] THERMOSTABLE DNA POLYMERASES HAVING REDUCED DISCRIMINATION AGAINST RIBO-NTPS

[75] Inventors: David Harrow Gelfand, Oakland; Lisa Vivian Kalman, San Francisco; Fred Lawrence Reichert, Oakland, all of Calif.

[73] Assignee: Roche Molecular Systems, Inc., Pleasanton, Calif.

[21] Appl. No.: 08/906,484

[22] Filed: Aug. 5, 1997

Related U.S. Application Data

[60] Provisional application No. 60/023,376, Aug. 6, 1996.
[51] Int. Cl.⁶ .............................. C12P 19/34; C12N 9/12; C07H 21/04
[52] U.S. Cl. .......................... 435/91.2; 435/194; 536/23.2
[58] Field of Search ................................... 435/194, 91.2; 536/23.2

[56] References Cited

U.S. PATENT DOCUMENTS

| | | | |
|---|---|---|---|
| 4,889,818 | 12/1989 | Gelfand et al. | 435/194 |
| 5,466,591 | 11/1995 | Abramson et al. | 435/194 |
| 5,614,365 | 3/1997 | Tabor et al. | 435/6 |

OTHER PUBLICATIONS

Berg et al., 1963, *Informational Macromolecular*, NY Academic Press:467–483.
Van De Sande et al., 1972, *J. Biol. Chem.* 247 (19):6140–6148.
Sanger et al., 1977, *Proc. Natl. Acad. Sci.* 74:5463.
Barnes, 1978, *J. Mol. Biol.* 119:83–99.
Ludwig, 1986, *Biophosphates and Their Analogues*, Elsevier.
Parvin et al., 1986, *DNA* 5 (2):167–171.
Nakamaye, 1988, *Nucleic Acids Research* 16 (21):9947–9959.
Murray, 1989, *Nucleic Acids Research* 17 (21):8889.
Lee et al., 1992, *Nucleic Acids Research* 20 (10):2471–2483.
Polesky, 1992, *J. Biol. Chem.*, 267 (12):8417–8428.
Akhmetzjanov and Vakhitov, 1992, *Nucleic Acids Research* 20 (21): 5839.
Walder et al., 1993, *Nucleic Acids Research* 21 (18):4339–4343.
Donlin and Johnson, 1994, *Biochemistry* 33:14908–14917.
Sousa and Padilla, 1995, *EMBO J.* 14 (18):4609–4621.
Delarue et al. "An Attempt to Unify the Structure of Polymerases", *Prot. Eng.* 3(6):461–467, 1990.

*Primary Examiner*—Robert A. Wax
*Assistant Examiner*—Einar Stole
*Attorney, Agent, or Firm*—Douglas A. Petry

[57] ABSTRACT

Modified thermostable DNA polymerases having enhanced efficiency for incorporating unconventional nucleotides, such as ribonucleotides, into DNA products, are advantageous in many in vitro synthesis applications. Such enzymes are particularly useful for use in nucleic acid sequencing protocols and provide novel means for DNA sequence analysis. Genes encoding the modified enzymes and methods for their production and use offer cost and efficiency advantages for DNA sequencing.

25 Claims, No Drawings

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 4
            (D) OTHER INFORMATION: /label= Xaa
                /note= "wherein Xaa is any amino acid but not Glu"

(ix) FEATURE:
            (A) NAME/KEY: Peptide
            (B) LOCATION: 7
            (D) OTHER INFORMATION: /label= Xaa
                /note= "wherein Xaa is Ile or Val"

(xi) SEQUENCE DESCRIPTION: SEQ ID NO:1:

Ser Gln Ile Xaa Leu Arg Xaa
1               5

(2) INFORMATION FOR SEQ ID NO:2:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 7
            (D) OTHER INFORMATION: /label= Xaa
                /note= "wherein Xaa is Ile or Val"

(xi) SEQUENCE DESCRIPTION: SEQ ID NO:2:

Ser Gln Ile Glu Leu Arg Xaa
1               5

(2) INFORMATION FOR SEQ ID NO:3:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Ser Gln Ile Glu Leu Arg Val
1               5

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Ser Gln Ile Glu Leu Arg Ile
1               5

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Leu Asp Tyr Ser Gln Ile Glu Leu Arg Val Leu Ala His Leu Ser
1               5                   10                  15
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu Asp Tyr Ser Gln Ile Gly Leu Arg Val Leu Ala His Leu Ser
1               5                   10                  15
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CGCCATTCGC CATTCAG                                               17

(2) INFORMATION FOR SEQ ID NO:8:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

GTGGATCGTC TCCGCGGACT ACTCCCAAAT AGGCCTACGT ATCCTCGCCC ATCTCA     56

(2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

ATGGGCGAGG ATACGTAGGC CTATTTGGGA GTAGTCCGCG GAGACGATCC ACCAGT     56

(2) INFORMATION FOR SEQ ID NO:10:

```
       (i) SEQUENCE CHARACTERISTICS:
           (A) LENGTH: 18 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:10:

GAAAGGAGCG GGCGCTAG                                                      18
```

THERMOSTABLE DNA POLYMERASES HAVING REDUCED DISCRIMINATION AGAINST RIBO-NTPS

This application claims benefit of U.S. Provisional Application Ser. No. 60/023,376, filed on Aug. 6, 1996.

FIELD OF THE INVENTION

The present invention relates to thermostable DNA polymerases which have enhanced efficiency for incorporating ribonucleoside triphosphates. The invention provides methods and means for isolating such polymerases. The enzymes of the invention are useful for many applications and in particular for nucleic acid sequencing applications. Thus, the invention also provides improved methods for nucleic acid sequence analysis.

BACKGROUND OF THE INVENTION

DNA sequencing generally involves the generation of four populations of single-stranded DNA fragments having one defined terminus and one variable terminus. The variable terminus generally terminates at specific nucleotide bases (either guanine (G), adenine (A), thyminine (T), or cytosine (C)). The four different sets of fragments are each separated on the basis of their length, one procedure being on a high resolution polyacrylamide gel; each band on the gel corresponds to a specific nucleotide in the DNA sequence, thus identifying the positions in the sequence.

A frequently used DNA sequencing method is the dideoxy or chain-terminating sequencing method, which involves the enzymatic synthesis of a DNA strand (Sanger et al., 1977, *Proc. Natl. Acad. Sci. USA* 74:5463, which is incorporated herein by reference). Four separate syntheses are generally run, each reaction being caused to terminate at a specific base (G, A, T, or C) via incorporation of an appropriate chain-terminating nucleotide, such as a dideoxynucleotide. The reaction products are easy to interpret since each lane corresponds only to either G, A, T, or C.

In the dideoxy chain-terminating method a short single-stranded primer is annealed to a single-stranded template. The primer is elongated at its 3' end by the incorporation of deoxynucleotides (dNTPs) until a dideoxynucleotide (ddNTP) is incorporated. When a ddNTP is incorporated, elongation ceases at that base. However, to assure fidelity of DNA replication, DNA polymerases have a very strong bias for incorporation of their normal substrates, dNTPs, and against incorporation of nucleotide analogues, referred to as unconventional nucleotides. In the case of DNA synthesis, ribonucleotides (rNTPs) are considered unconventional nucleotides, because, like ddNTPs, rNTPs are not the normal in vivo substrate of a DNA polymerase. In the cell this property attenuates incorporation of abnormal bases such as deoxyinosine triphosphate (dITP) or rNTPs in a growing DNA strand.

Two frequently used automated sequencing methodologies are dye-primer and dye-terminator sequencing. These methods are suitable for use with fluorescent label moieties. Although sequencing can also be done using radioactive label moieties, fluorescence-based sequencing is increasingly preferred. Briefly, in dye-primer sequencing, a fluorescently labeled primer is used in combination with unlabeled ddNTPs. The procedure requires four synthesis reactions and up to four lanes on a gel for each template to be sequenced (one corresponding to each of the base-specific termination products). Following primer extension, the sequencing reaction mixtures containing dideoxynucleotide-incorporated termination products routinely are electrophoresed on DNA sequencing gel. Following separation by electrophoresis, the fluorescently-labeled products are excited with a laser at the bottom of the gel and the fluorescence is detected with an appropriate monitor. In automated systems, a detector scans the bottom of the gel during electrophoresis, to detect whatever label moiety has been employed, as the reactions pass through the gel matrix (Smith et al., 1986, *Nature* 321:674–679, which is incorporated herein by reference). In a modification of this method, four primers are each labeled with a different fluorescent marker. After the four separate sequencing reactions are completed, the mixtures are combined and the reaction is subjected to gel analysis in a single lane, and the different fluorescent tags (one corresponding to each of the four different base-specific termination products) are individually detected.

Alternatively, dye-terminator sequencing methods are employed. In this method, a DNA polymerase is used to incorporate dNTPs and fluorescently labeled ddNTPs onto the growing end of a DNA primer (Lee et al., 1992, *Nucleic Acid Research* 20:2471). This process offers the advantage of not having to synthesize dye-labeled primers. Furthermore, dye-terminator reactions are more convenient in that all four reactions can be performed in the same tube. Modified thermostable DNA polymerases having reduced discrimination against ddNTPs have been described (see European Patent Application, Publication No. EP-A-655 506 and U.S. patent application Ser. No. 08/448,223). An exemplary modified thermostable DNA polymerase is the mutated form of the DNA polymerase from *T. aquaticus* having a tyrosine residue at position 667 (instead of a phenylalanine residue), i.e. is a so called F667Y mutated form of Taq DNA polymerase. AmpliTaq® FS, manufactured by Hoffmann-La Roche and marketed through Perkin Elmer, reduces the amount of ddNTP required for efficient nucleic acid sequencing of a target by hundreds to thousands-fold. AmpliTaq® FS is a mutated form of the DNA polymerase from *T. aquaticus* having the F667Y mutation and additionally an aspartic acid residue at position 46 (instead of a glycine residue; G46D mutation).

There is a need for thermostable DNA polymerases that enable alternative nucleic acid synthesis methods for accurate and cost effective nucleic acid DNA sequence analysis. Fluorescence-based methods that do not require the use of dideoxynucleotides would be desirable. The present invention addresses these needs.

SUMMARY OF THE INVENTION

The present invention provides template-dependent thermostable DNA polymerase enzymes that comprise the amino acid sequence S Q I X L R V/I (SEQ ID NO: 1), wherein "X" is any amino acid residue but not a glutamic acid residue. In the three letter code for amino acids this amino acid sequence is represented as SerGlnIleXaaLeuArgXaa (SEQ ID NO: 1), whereby "Xaa" at position 4 of this sequence is any amino acid residue but not a glutamic acid residue (Glu) and "Xaa" at position 7 of this sequence is a valine residue (Val) or an isoleucine residue (Ile). These enzymes have reduced discrimination against incorporation of ribonucleotides in comparison to previously known thermostable polymerases. In a growing DNA strand ribonucleotides are unconventional nucleotides. Thus, in a first aspect, the novel enzymes of the invention incorporate unconventional base analogues, such as ribonucleotides, into a growing DNA strand, several orders of magnitude more efficiently than previously identified thermostable DNA synthesizing enzymes. Genes encoding these enzymes are also provided by the present invention, as well as recombinant expression vectors for providing large amounts of purified enzymes.

By the present invention, a region of criticality within thermostable DNA polymerases is identified, which enhances the efficiency of the polymerase's ability to incorporate ribonucleotides while retaining the ability to faithfully incorporate deoxyribonucleotides. This region of criticality allows the synthesis of an RNA or an RNA/DNA chimeric or hybrid strand from a DNA template. This region of criticality can be introduced by, for example, site-specific mutagenesis, to provide the advantages of the invention.

In another aspect, the invention provides improved methods for determining the sequence of a target nucleic acid, wherein the need for chain-terminating ddNTPs is eliminated. By the improved methods provided herein, ribonucleotides (rNTPs) are incorporated into primer extension products. Because the subject enzymes accurately and efficiently incorporate either rNTPs or dNTPs, sequencing reactions can utilize mixtures of both nucleotides. Following primer extension, newly synthesized oligonucleotide products can be cleaved at the incorporated rNTPs, providing a population of fragments suitable for fractionation and sequence analysis by conventional means, such as gel electrophoresis. These methods utilize the novel thermostable polymerase enzymes provided herein. Thus, in this aspect the invention provides thermostable DNA polymerase enzymes which are characterized in that the polymerase comprises the critical motif (SEQ. ID NO: 1), S Q I X L R V/I, wherein "X" is any amino acid residue but not a glutamic acid residue, or as represented in the three letter code for amino acids as SerGlnIleXaaLeuArgXaa, wherein "Xaa" at position 4 can be any amino acid residue but not a glutamic acid residue (Glu) and "Xaa" at position 7 is a valine residue (Val) or an isoleucine residue (Ile).

In another aspect of the invention, the polymerases described herein provide means for incorporating ribonucleotides or ribonucleotide analogues containing a hydroxyl group, or other substitution, at the 2' position which, in comparison, is absent in conventional deoxyribonucleotides. In a preferred embodiment of the invention, the ribonucleotide to be incorporated may be a chain-terminating base analogue, such as 2'-hydroxy-3' deoxy rATP (cordycepin triphosphate) which is a "riboterminator" analogue of ATP, or a non-chain-terminating nucleotide such as a rNTP. These nucleotides can be differentially labeled, providing alternatives to the conventional use of dideoxynucleotides for DNA sequencing applications.

In another aspect of the invention, mutant thermostable polymerase enzymes are provided which are characterized by the ability to more efficiently incorporate unconventional nucleotides, particularly ribonucleotides, than the corresponding wild-type enzymes. Thus, in this aspect the invention provides recombinant thermostable DNA polymerase enzymes which are each characterized in that (a) in its native form the polymerase comprises the amino acid sequence (SEQ ID NO: 2), S Q I E L R V/I or as represented in the three letter code for amino acids SerGlnIleGluLeuArgXaa wherein "Xaa" at position 7 of this sequence is a valine residue (Val) or an isoleucine residue (Ile); (b) the amino acid sequence is mutated in the recombinant enzyme; and (c) the recombinant enzyme has reduced discrimination against incorporation of ribonucleotides and ribonucleotide analogues in comparison to the native form of said enzyme.

In another aspect of the invention, the polymerases of the invention provide a convenient means of fragmenting amplification products and primer extension products. Such fragmented products may be useful in hybridization-based methodologies and a variety of sequence detection strategies.

These enzymes, and genes encoding these enzymes, provide additional aspects of the invention which are compositions for use in DNA sequencing reactions that comprise a mixture of conventional nucleotides and at least one ribonucleotide or ribonucleotide analogue. In a preferred embodiment of the invention, the unconventional nucleotide is a ribonucleotide, and the ribonucleotide concentration is less than the concentration of the corresponding deoxyribonucleotide, i.e., the rNTP:dNTP ratio is 1:1 or less. The enzymes of the invention are also suitable for commercialization in kit formats, which may also include any of the following additional elements, such as dNTPs, rNTPs, buffers or primers.

DETAILED DESCRIPTION OF THE INVENTION

The present invention provides novel and improved compositions which are modified thermostable DNA polymerases. Enzymes of the invention more efficiently incorporate unconventional nucleoside triphosphates than corresponding wild-type enzymes. DNA sequences encoding these modified enzymes and vectors for expressing the modified proteins, are also provided. The enzymes of the invention enable the practice of novel DNA sequencing methods which are advantageous over prior DNA sequencing procedures.

To facilitate understanding of the invention, a number of terms are defined below. The term "conventional" when referring to nucleic acid bases, nucleoside triphosphates, or nucleotides refers to those which occur naturally in the polynucleotide being described (i.e., for DNA these are DATP, dGTP, dCTP and dTTP). Additionally, c7dGTP and dITP are frequently utilized in place of dGTP (although incorporated with lower efficiency) in in vitro DNA synthesis reactions, such as sequencing. Collectively, these may be referred to as dNTPs.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full-length gene sequence or by any portion of the coding sequence so long as the enzymatic activity is retained.

The term "host cell(s)" refers to both single cellular prokaryote and eukaryote organisms such as bacteria, yeast, and actinomycetes and single cells from higher order plants or animals when being grown in cell culture.

As used herein, the term "DNA sequencing reaction mixture" refers to a reaction mixture that comprises elements necessary for a DNA sequencing reaction. Thus, a DNA sequencing reaction mixture is suitable for use in a DNA sequencing method for determining the nucleic acid sequence of a target, although the reaction mixture may initially be incomplete, so that the initiation of the sequencing reaction is controlled by the user. In this manner, the reaction may be initiated once a final element, such as the enzyme, is added, to provide a complete DNA sequencing reaction mixture. Typically, a DNA sequencing reaction will contain a buffer, suitable for polymerization activity, nucleoside triphosphates and at least one unconventional nucleotide. The reaction mixture also may contain a primer suitable for extension on a target by a polymerase enzyme, a polymerase and a target nucleic acid. Either the primer or one of the nucleotides is generally labeled with a detectable moiety such as a fluorescent label. Generally, the reaction is a mixture that comprises four conventional nucleotides and at least one unconventional nucleotide. In a preferred embodiment of the invention, the polymerase is a thermostable DNA polymerase and the unconventional nucleotide is a ribonucleotide.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; the triester method of Matteucci et al., 1981, *J. Am. Chem. Soc.* 103:3185–3191; automated synthesis methods; or the solid support method of U.S. Pat. No. 4,458,066, which publications are each incorporated herein by reference.

The term "primer" as used herein refers to an oligonucleotide, whether natural or synthetic, which is capable of acting as a point of initiation of synthesis when placed under conditions in which primer extension is initiated. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur.

A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISAS), biotin, or haptens and proteins for which antisera or monoclonal antibodies are available.

The term "thermostable polymerase," refers to an enzyme which is stable to heat, is heat resistant and retains sufficient activity to effect subsequent primer extension reactions when subjected to the elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are incorporated herein by reference. As used herein, a thermostable polymerase is suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid strand.

The term "unconventional" or "modified" when referring to a nucleic acid base, nucleoside triphosphate, or nucleotide, includes modification, derivations, or analogues of conventional bases, or nucleotides that naturally occur in DNA. More particularly, as used herein, unconventional nucleotides are modified at the 2' position of the ribose sugar in comparison to conventional dNTPs. Thus, although for RNA the naturally occurring nucleotides are ribonucleotides (i.e., ATP, GTP, CTP, UTP collectively rNTPs), because these nucleotides have a hydroxyl group at the 2' position of the sugar, which, by comparison is absent in dNTPs, as used herein, ribonucleotides are unconventional nucleotides. Ribonucleotide analogues containing substitutions at the 2' position, such as 2'-fluoro or 2'-amino, are within the scope of the invention. Additionally, ribonucleotide analogues may be modified at the 3' position, for example, wherein the normal hydroxyl is replaced with a hydrogen (3' deoxy), providing a ribonucleotide analogue terminator. Such nucleotides all are included within the scope of the term "unconventional nucleotides."

Since DNA is conventionally composed of dNTPs, incorporation of an rNTP would be unconventional and thus a rNTP would be an unconventional base. Consequently, in a preferred embodiment of the invention, for DNA primer extension methods including DNA sequencing methods, nucleic acid products contain both conventional and unconventional nucleotides, and predominantly comprise conventional nucleotides which are dNTPs.

Unconventional bases may be fluorescently labeled with, for example, fluorescein, or rhodamine; non-fluorescently labeled with, for example biotin; isotopically labeled with, for example, $^{32}P$, $^{33}P$, or $^{35}S$; or unlabeled.

In order to further facilitate understanding of the invention, specific thermostable DNA polymerase enzymes are referred to throughout the specification to exemplify the invention; however, these references are not intended to limit the scope of the invention. In a preferred embodiment the thermostable enzymes of the invention are utilized in a variety of nucleic acid sequencing methods, although the novel thermostable polymerases described herein may be used for any purpose in which such enzyme activity is necessary or desired.

The thermostable polymerases of the invention are characterized in that each contains the critical motif SerGlnIleXaaLeuArgXaa (SEQ ID NO: 1), whereby "Xaa" at position 4 of this sequence is any amino acid residue but not a glutamic acid residue (Glu) and "Xaa" at position 7 of this sequence is a valine residue (Val) or an isoleucine residue (Ile). Genes encoding thermostable polymerases which have a glutamic acid residue at the position 4 of the said motif can be modified as described herein to provide suitable modified polymerase enzymes. Said modified thermostable polymerase enzymes are characterized in that in comparison to the corresponding native or wild-type enzymes, they have a modification in the amino acid sequence motif SerGlnIleGluLeuArgXaa (SEQ ID NO: 2), wherein "Xaa" at position 7 of this sequence is a valine residue (Val) or an isoleucine residue (Ile), i.e. said motif has been modified by a replacement of the glutamic acid residue at position 4 by another amino acid residue. The critical motif of a thermostable DNA polymerase provided by the present invention is shown below using the conventional three-letter amino acid code (Lehninger, Biochemistry, New York, N.Y., Worth Publishers Inc., 1970, page 67, which is incorporated herein by reference).

SEQ ID NO: 1 SerGlnIleXaaLeuArgXaa,
wherein "Xaa" at position 4 is any amino acid residue but is not a glutamic acid residue (Glu) and "Xaa" at position 7 is a valine residue (Val) or an isoleucine residue (Ile).

Both, gene sequences encoding and proteins containing this critical amino acid sequence, wherein Xaa at position 4 is not a glutamic acid residue (Glu), provide a polymerase having decreased discrimination against rNTPs, and are within the scope of the invention. Within the critical motif, additional modifications may be made with respect to other amino acid residues in this critical motif, preferably with respect to an amino acid residue selected from the group of glutamine (Gln or Q), leucine (Leu or L), or arginine (Arg or R).

The present invention is suitable for preparing thermostable DNA polymerase enzymes with advantageous properties by particular modification of the gene sequence encoding a thermostable DNA polymerase. In a preferred embodiment of the invention, the gene sequence and encoded enzyme are derived from a species of the genus Thermus, although non-Thermus eubacteria are included within the scope of the invention as described in detail below. Analogously, in view of the highly conserved nature of the now identified motif, novel thermostable DNA polymerases may be identified based upon their homology to, for example, Taq polymerase. Such polymerases are within the scope of the present invention, as long as their amino acid sequence comprises the S Q I X L R V/I (SEQ ID NO: 1) motif, wherein X is any amino acid residue but not glutamic acid residue and which amino acid sequence displays at least 45% and most preferably greater than 80% overall homology (sequence identity) in comparison to the amino acid sequence of the native Taq polymerase. The full-length sequence of said Taq polymerase is provided in WO 89/06691 and accessible under accession No. P90556 in the GENESEQ patent sequence data bank or under accession No. M26480 in the EMBL sequence data bank and under accession No. A33530 in the PIR sequence data bank.

Exemplary thermostable DNA polymerases of the present invention are recombinant derivatives of the native polymerases from the organisms listed in Table 1 below. Table 1 indicates the particular sequence of the critical motif and the position of the "X" residue for each of these native polymerases. Because each thermostable DNA polymerase is unique, the amino acid position of the critical motif is distinct for each enzyme. For those polymerases listed below, the amino acid residue in the "X" position of the sequence corresponding to the critical S Q I X L R V/I (SEQ ID NO: 1) motif is glutamic acid. The preferred polymerases of the present invention have a molecular weight in the range of 85,000 to 105,000, more preferably between 90,000 to 95,000. The amino acid sequence of these polymerases consists of about 750 to 950 amino acid residues, preferable between 800 and 900 amino acid residues. The polymerases of the present invention may also consist of about 540 or more amino acids and comprise at least the polymerase domain, and a portion corresponding to the 3' to 5' exonuclease domain and possibly parts of the 5' to 3' exonuclease domain, which is contained on the first one-third of the amino acid sequence of many full-length thermostable polymerase enzymes.

For thermostable DNA polymerases not shown in Table 1, identifying the appropriate glutamic acid for modification is simple once the critical motif or consensus motif in the amino acid sequence is identified.

Regardless of the exact position within a thermostable DNA polymerase, mutation of the glutamic acid (E) residue within the sequence amino acid motif S Q I E L R V/I (Sequence ID No 2) of the polymerase domain serves to provide a thermostable polymerase having the ability to efficiently incorporate unconventional nucleotides. In a preferred embodiment, the glutamic acid is replaced by an amino acid having an uncharged polar R group such as serine, cysteine, threonine or by an amino acid having a nonpolar R group such as alanine. In a most preferred embodiment, the glutamic acid residue is replaced by glycine (G). Amino acid and nucleic acid sequence alignment programs are readily available from the Genetics Computer Group, 575 Science Drive, Madison, Wis. Given the particular motif identified herein, these programs, including, for example, "GAP," "BESTFIT," and "PILEUP," serve to assist in the identification of the exact sequence region to be modified.

TABLE 1

| Organism | Seq ID No. | Amino Acid Consensus Motif | Position of Glutamic Acid |
|---|---|---|---|
|  | 1 | S Q I X L R V/I* |  |
| Thermus aquaticus (Taq) | 3 | S Q I E L R V | 615 |
| Thermus caldophilus (Tca) |  | S Q I E L R V | 617 |
| Thermus thermophilus (Tth) |  | S Q I E L R V | 617 |
| Thermus flavus (Tfl) |  | S Q I E L R V | 616 |
| Thermus filiformis (Tfi) |  | S Q I E L R V | 613 |
| Thermus specie sps17 |  | S Q I E L R V | 613 |
| Thermus specie Z05 |  | S Q I E L R V | 617 |
| Thermotoga maritima (Tma) | 4 | S Q I E L R I | 678 |
| Thermotoga neapolitana (Tne) |  | S Q I E L R I | 678 |
| Thermosipho africanus (Taf) |  | S Q I E L R V | 677 |
| Anaerocellum thermophilum (Ath) |  | S Q I E L R I | 632 |
| Bacillus caldotenax (Bca) |  | S Q I E L R V | 659 |
| Bacillus stearothermophilus (Bst) |  | S Q I E L R V | 658, 661, or 736 |

*wherein "X" is any amino acid residue but not a glutamic acid residue. The full nucleic acid and amino acid sequence for each of Taq, Tth, Z05, ps17, Tma, and Taf polymerase has published in U.S. Pat. No. 5,466,591 and is incorporated herein by reference. The sequences for the DNA polymerases from Tca, Tfl, Tne, Ath, Bca, and Bst have been published as follows: Tca in the EMBL sequence data bank under Accession No. U62584 (see also Kwon, 1997, *Mol. Cells* 7(2): 264–271); Tfl in Akhmetzjanov and Vakhitov, 1992, *Nucleic Acids Research* 20(21):5839; Tne in WO 97/09451 and WO 96/41014; Ath in the EMBL sequence data bank under Accession No. X98575 (for details on the Ath strain see Rainey et al., 1993, *J. Bacteriol.* 175 (15): 4772–2779; Bst in Uemori et al., 1993, *J. Biochem.* 113:401–410 and under EMBL sequence data bank Accession No. U23149 (see also Phang et al., 1995, *Gene* 163:65–68). Bst polymerase amino acid sequences comprising an E in the critical motif at position 658 are also provided by Japanese Patent publication JP 05/304 964A, European Patent publication No. EP-A-699,760, and Aliotta et al., 1996, *Genet. Anal.* 12: 185–195; the sequence is also available from the EMBL sequence data bank under Accession No. U33536. The sequence as published in *Gene* 163: 65–68 (1995), contains the "E" of the critical motif at residue number 661. Bca in Uemori et al., 1993, *J. Biochem.* 113:401–410 and under EMBL sequence data bank Accession No. D12982. The thermostable DNA polymerase from *Thermus filiformis* (see *FEMS Microbiol. Lett.* 22: 149–153, 1994; also available from ATCC Deposit No. 43280) can be recovered using the methods provided in U.S. Pat. No. 4,889,818, as well as based on the sequence information provided in Table 1.

As Table I demonstrates, the critical motif is remarkably conserved among the thermostable DNA polymerases. Where "X" is a glutamic acid residue, alteration of the gene encoding the polymerase provides the enzyme of the invention, which readily incorporates rNTPs in comparison to, for example, Taq polymerase wherein the critical motif is not modified. Consequently, the invention relates to a class of enzymes which also includes, for example, the thermostable DNA polymerase, and corresponding gene and expression vectors from *Thermus oshimai* (Williams RA, et al. *Int J Syst Bacteriol* 46 (2): 403–408, April 1996); *Thermus silvanus* and *Thermus chliarophilus* (Tenreiro S, et al. *Int. J. Syst. Bacteriol* 45 (4): 633–639, October 1995); *Thermus scotoductus* (Tenreiro S et al. *Res Microbiol* 146 (4): 315–324, May 1995); *Thermus brockianus* (Munster, M. J. J. *Gen Microbiol*. 132: 1677, 1986); *Thermus ruber* ATCC 35948, (L. G. Loginova 21. *Int. J. Syst. Bacteriol.* 34: 498–499, 1984); *Thermotoga elfii* (Ravot et al. 1995 *Int. J. Syst. Bacteriol.* 45:312-DSM 9442); and *Thermotoga thermarum* (Windberger et al. 1992 *Int. J. Syst. Bacteriol.* 42:327 DSM 5069) which are each incorporated herein by reference.

In a preferred embodiment of the invention, the critical motif to be modified is within the amino acid sequence LeuAspTyrSerGlnIleGluLeuArgValLeuAlaHisLeuSer (SEQ ID NO: 5). Thus, one aspect of the invention involves the generation of thermostable DNA polymerase mutants displaying greatly increased efficiency for incorporating unconventional nucleotides in a template-dependent manner. In a particularly preferred embodiment, the polymerase sequence comprises LeuAspTyrSerGlnIleGlyLeuArgValLeuAlaHisLeuSer (SEQ ID NO: 6).

Such thermostable DNA polymerases are surprisingly suitable in processes such as DNA sequencing, DNA directed RNA synthesis, and in vitro synthesis of rNTP substituted DNA.

The production of thermostable DNA polymerases with enhanced efficiency for incorporating unconventional bases may be accomplished by processes such as site-directed mutagenesis. See, for example, Sambrook et al., *Molecular Cloning: A Laboratory Manual*, Cold Spring Harbor, 1989, second edition, Chapter 15.51, "Oligonucleotide-Mediated Mutagenesis," which is incorporated herein by reference. For example, a mutation of "A" to a "G" in the second position of the codon encoding glutamic acid at residue 615 in the *Thermus aquaticus* (Taq) DNA polymerase gene sequence results in more than a 500-fold increase in the efficiency of incorporation of unconventional nucleotides, as defined herein, while retaining the enzyme's ability to mediate PCR in the presence of conventional nucleotides, i.e., dNTPs. In Taq DNA polymerase this particular mutation results in an amino acid change of E (glutamic acid) to G (glycine). Although this particular amino acid change significantly alters the ability of the enzyme to incorporate unconventional nucleotides, it is expected that the specific change of E to G is not critical to the invention. Other amino acid substitutions which replace E615 are within the scope of the invention, although E615G represents a preferred embodiment. Thus, a critical aspect of the invention is that the fourth amino acid residue in the motif of Seq. ID No. 1 is not a glutamic acid residue.

Site-directed mutagenesis is generally accomplished by site-specific primer-directed mutagenesis. This technique is now standard in the art and is conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. Alternatively, "recombinant PCR" methods can be employed (Innis et al. editors, *PCR Protocols*, San Diego, Academic Press, 1990, Chapter 22, Entitled "Recombinant PCR", Higuchi, pages 177–183).

As demonstrated in Table I, the glutamic acid within the critical motif of Taq polymerase is conserved in other thermostable DNA polymerases but may be located at a different position. A mutation of the conserved glutamic acid within Seq ID No. 2 of Thermus species thermostable DNA polymerases and the related Thermotoga, Thernosipho, Bacillus, and Anaerocellum species DNA polymerases, will have a similar enhancing effect on the ability of the polymerase to efficiently incorporate unconventional nucleotides in comparison to Taq polymerase comprising Seq. ID No. 2. Mutations of the glutamic acid residue within the critical motif in other thermostable DNA polymerases can be accomplished utilizing the principles and techniques used for site-directed mutagenesis. There are several sequence submissions for *Bacillus stearothennophilus* DNA polymerase in the GeneBank, or SwissProt/PIR databases. Although these sequences are highly related, but somewhat different from one another, each contains the identical S Q I E L R V (Seq ID No. 3) critical motif sequence.

Based on the publicly available amino acid and nucleic acid sequence information for thermostable DNA polymerases as described herein, it is also possible to construct, by conventional recombinant methodologies, chimeric polymerases which provide enzymes having sequences and/or properties from more than one source. U.S. Pat. Nos. 5,466, 591 and 5,374,553 describe methods for exchanging the various functional segments of thermostable polymerases, such as the 5' to 3' exonuclease domain, the 3' to 5' exonuclease domain and the polymerase domain to provide novel enzymes. Chimeric thermostable polymerase enzymes may comprise a 5' to 3' exonuclease domain, a 3' to 5' exonuclease domain and a polymerase domain, whereby one domain is derived from a different polymerase and whereby the polymerase domain comprises the critical motif sequence S Q I X L R V/I (SEQ ID NO: 1), wherein "X" is any amino acid residue but not a glutamic acid residue. Examples for such a chimeric molecules are Taq/Tma chimeric enzymes which are composed as specified in Table 2. As indicated in this Table the polymerase domain of these Taq/Tma chimeric enzymes contains the mutation in the critical motif specified above.

TABLE 2

|  | 5' to 3' exonuclease domain | 3' to 5' exonuclease domain | polymerase domain |
| --- | --- | --- | --- |
| Taq | aa. 1–289 | aa. 290–422 | aa. 423–832 |
| Tma | aa. 1–291 | aa. 292–484 | aa. 485–893 |
| Taq/Tma | aa. 1–289 (Taq) | aa. 292–484 (Tma) | aa. 423–832 (Taq) with E615G mutation |
| Taq/Tma | aa. 1–289 (Taq) | aa. 292–484 (Tma) | aa. 485–893 (Tma) with E678G mutation |

However, in a preferred embodiment of the invention, portions of a domain, rather than an entire functional domain are exchanged or added to a polymerase gene sequence. For example, this type of chimeric molecule is described herein in Example VII, wherein a Taq/Tma chimeric enzyme is provided that is encoded by a chimeric gene containing a mutation in the codon encoding the amino acid corresponding to position 678, in accord with Table 1.

Plasmid pC1 has been deposited with the ATCC, on Jul. 17, 1996, and given Accession No. 98107. This plasmid contains a gene encoding a thermostable DNA polymerase that is mutated at the codon encoding E615G such that glutamic acid is replaced with glycine in the resulting polypeptide. This deposit provides alternative means for providing thermostable DNA polymerases having an enhanced efficiency for incorporating unconventional nucleotide analogues. Example I illustrates the use of flanking restriction sites suitable for subcloning the E615G mutation to create other thermostable DNA polymerase enzymes. Alternatively, because the complete gene sequence for numerous thermostable DNA polymerases are known, other means for introducing a mutation at the codon encoding E 615, such as by restriction digestion and fragment replacement, or by site specific in vitro mutagenesis, are readily available to those of skill in the art, having the availability of ATCC deposits and the sequence information provided herein.

The modified gene or gene fragment can be recovered from the plasmid, or phage by conventional means and ligated into an expression vector for subsequent culture and purification of the resulting enzyme. Numerous cloning and expression vectors, including mammalian and bacterial systems, are suitable for practicing the invention, and are described in, for example, Sambrook et al., *Molecular Cloning: A Laboratory Manual*, second edition, Cold Spring Harbor, 1989. For convenience, the present invention is exemplified utilizing the lambda derived PL promoter (Shimatake et al., 1981, *Nature* 292:128). Use of this promoter is specifically described in U.S. Pat. Nos. 4,711,845 and 5,079,352, which are incorporated herein by reference.

The thermostable DNA polymerases of the present invention are generally purified from microorganisms such as e.g. *E. coli* which have been transformed with an expression vector operably linked to a gene encoding a wild-type or modified thermostable DNA polymerase. An example for a suitable host microorganisms is the *E. coli* strain DG116 described by Lawyer et al., 1993, *PCR Methods and Applications* 2:275–287, which strain is also available from the American Type Culture Collection under Accession No. ATCC 53601. Methods for purifying the thermostable polymerase are also described in, for example, Lawyer et al., 1993, *PCR Methods and Applications* 2:275–287.

Those of skill in the art will recognize that the above thermostable DNA polymerases with enhanced efficiency for incorporating unconventional nucleotides are most easily constructed by recombinant DNA techniques. When one desires to produce one of the enzymes of the present invention, or a derivative or homologue of those enzymes, the production of a recombinant form of the enzyme typically involves the construction of an expression vector, the transformation of a host cell with the vector, and culture of the transformed host cell under conditions such that expression will occur. Means for preparing expression vectors, transforming and culturing transformed host cells are well known in the art and are described in detail in, for example, Sambrook et al., 1989, supra.

The present invention provides thermostable DNA polymerases suitable for use with ribonucleoside triphosphates for numerous applications including nucleic acid amplification, detection and DNA sequencing methods. The use of ribonucleotides in sequencing avoids the high cost of chain-terminating analogues, such as ddNTPs and importantly, facilities the preparation of novel amplification products suitable not only for DNA sequence analysis but also other types of analysis such as electrophoresis or hybridization without the need to conduct subsequent DNA sequencing reactions.

Pyrophosphatase has been shown to enhance sequencing results using both mesophilic polymerases and thermostable DNA polymerase by decreasing the amount of pyrophosphorolysis as extension products accumulate. Indeed, prior cycle sequencing methods require that the additional enzyme is included in the sequencing reaction. However, a very useful and advantageous aspect of the present invention is that pyrophosphatase is not required for DNA sequencing. Thus, use of the novel enzymes provided herein eliminates the need for the additional expense of adding a second enzyme into the sequencing reaction mixture.

Thus, by use of the present enzymes, the amplification and sequencing reactions are combined saving time and materials, as well as simplifying the overall analysis. These advantages, and others, are available primarily because the incorporation of both conventional nucleotides as well as ribonucleotides and ribonucleotide analogues into a primer extension product provides an RNA/DNA chimeric strand that is susceptible to hydrolysis of the RNA. The treatment does not affect the DNA backbone and provides a population of nucleic acid fragments each terminating at the position where a ribonucleotide was inserted in place of the corresponding DNTP. Hydrolysis is readily accomplished by various means including but not limited to alkali, heat or enzymatic treatment with an RNAse (Vogel et al., editors, *Informational Macromolecular*, New York, Academic Press, 1963, Chapter by Berg et al., Entitled "The Synthesis of Mixed Polynucleotide Containing ribo- and deoxyribonucleotide by Purified Preparation of DNA Polymerase from *E. coli*", pages 467–483).

In a preferred embodiment, the present invention provides novel and improved compositions particularly useful for DNA sequencing methods. The novel enzymes described herein are advantageous in nucleic acid sequencing methods, using either dye-terminators or dye-primers, as well as other sequencing methods. As previously described, chain termination methods generally require template-dependent primer extension in the presence of chain-terminating nucleotides, resulting in a distribution of partial fragments which are subsequently separated by size. Standard dideoxy sequencing utilizes dideoxynucleoside triphosphates for chain termination and a DNA polymerase such as the Klenow fragment of *E. coli* Pol I (see Sanger et al., supra.).

Thus, the basic dideoxy sequencing procedure involves (i) annealing an oligonucleotide primer to a template; (ii) extending the primer with DNA polymerase in four separate reactions, each containing one labeled nucleotide, or a labeled primer, a mixture of unlabeled dNTPs, and one chain-terminating ddNTP; (iii) resolving the four sets of reaction products by means of, for example, high-resolution denaturing polyacrylamide/urea gel electrophoresis, capillary separation or by other resolving means; and (iv) producing an autoradiographic image of the gel that can be examined to infer the sequence. Alternatively, mass spectrometry methods or hybridization-based methods, using fluorescently labeled primers or nucleotides, can be used to derive DNA sequence information.

The availability of thermoresistant polymerases, such as Taq polymerase, has resulted in improved methods for sequencing (see U.S. Pat. No. 5,075,216, which is incorporated herein by reference) and modifications thereof referred to as "cycle sequencing." In cycle sequencing, cycles of heating and cooling are repeated allowing numerous extension products to be generated from each molecule of target (Murray, 1989, *Nucleic Acids Research* 17:8889, which is incorporated herein by reference). This asymmetric amplification of target sequences complementary to the template sequence, in the presence of dideoxy chain terminators, produces a family of extension products of all possible lengths.

Following denaturation of the extension reaction product from the DNA template, multiple cycles of primer annealing and primer extension occur in the presence of dideoxy terminators. Thermostable DNA polymerases have several advantages in cycle sequencing; they tolerate the stringent annealing temperatures which are required for specific hybridization of primer to nucleic acid targets as well as tolerating the multiple cycles of high temperature denaturation which occur in each cycle, i.e., 90–95° C. For this reason, various forms of AmpliTaq® DNA polymerase have been included in Taq cycle sequencing kits commercialized by Perkin Elmer, Norwalk, Conn.

Nevertheless, the property of Taq DNA polymerase, to discriminate against incorporation of unconventional nucleotides, such as ddNTPs, presents a problem when it is used for cycle sequencing, where ddNTPs or fluorescently labeled ddNTPs must be incorporated as chain terminators. Generally, prior to the present invention, DNA sequencing with thermostable DNA polymerases required a mixture of chain-terminating nucleotides, generally dideoxynucleotides, at high concentrations, to insure that a population of extension products would be generated representing all possible fragment lengths over a distance of several hundred bases. Frequently, to address this cost issue, protocols utilized very low concentrations of conventional dNTPs, making the reactions inefficient. These reaction mixtures, having a low DNTP concentration and a high ddNTP concentration, create an environment wherein the thermostable polymerase is essentially starved for nucleotide substrates.

Even with the advent of modified enzymes, such as AmpliTaq® DNA polymerase, FS, which allow the concentration of dNTPs to be increased to more optimal levels, the prior enzymes still rely on the presence of costly ddNTPs for DNA sequencing. In contrast, the present invention provides enzymes that not only allow the concentration of dNTPs to be increased, but avoid the high cost of ddNTPs by using, instead, rNTPs for incorporation into the growing strand. The ability of novel enzymes to efficiently effect partial ribonucleotide substitution facilitates the generation of DNA sequencing ladders in the absence of a separate reaction for incorporating a terminating nucleotide.

The choice of unconventional bases suitable for use in DNA sequencing methods was previously dictated by the ability of the thermostable DNA polymerase to incorporate analogues. Unfortunately, suitable analogues are costly. For example, the cost of ddNTPs is approximately 25× greater than the cost of either rNTPs or dNTPs. Because, prior thermostable DNA polymerases were unable to efficiently incorporate rNTPs in a template directed manner into a growing DNA strand, ribonucleotides, which are readily available and inexpensive, were not an option for use in DNA sequencing with a thermostable DNA polymerase. The present invention eliminates the need for ddNTPs in DNA sequencing reactions. Thus, in one aspect the invention provides methods for DNA sequencing analysis that are significantly less expensive than prior chain termination methods.

The presence of manganese in a primer extension reaction can influence the ability of a polymerase to accurately insert the correctly based paired nucleotide. Managese can be used to force incorrect base pairing or to ease the discrimination against insertion of a nucleotide analogue. Manganese has been used by researchers to induce mutagenesis in DNA replication or amplification procedures. Thus, manganese can affect the fidelity of a polymerization reaction, as well as the yield of a reaction. The resulting sequence may be incorrect or, in a DNA sequencing method, the resulting information may be ambiguous. The present methods do not require that manganese is included as the divalent cation in the sequencing reaction mixture to force the polymerase to insert an unconventional nucleotide. In contrast to prior DNA polymerases, the present invention identifies the critical motif within the polymerase domain for controlling the enzyme's ability to discriminate between 2' substituted and unsubstituted nucleotides without the need for manganese.

The enzymes of the invention do not require high concentrations of the unconventional base analogues for sequencing. Prior to the present invention unconventional base analogues and the corresponding conventional bases were generally present at a ratio (e.g., ddATP:dATP) ranging from approximately 1.3:1 to 24:1 for chain termination DNA sequencing methods. In comparison, the thermostable polymerases provided by the present invention allow the ratio of unconventional base analogues to conventional bases to be reduced from a hundred to several thousand fold. A rNTP:dNTP ratio of 1:1 or less, in combination with the novel enzymes provided herein, is sufficient for DNA sequence analysis. In a preferred embodiment of the invention, the rNTP:dNTP ratio is reduced to less than 1:8. The ratio of 2' substituted nucleotide to the corresponding natural dNTP may be as low as 1:80 or 1:200, depending on the particular experimental design and desired length of fragments.

Thus, because the present enzymes readily incorporate unconventional nucleotides, such as 2' substituted nucleotides, it is not necessary to force incorporation of the rNTP by using a high concentration of rNTP and a limiting concentration of the corresponding DNTP. Accordingly, the present methods enable the use of optimal concentrations of dNTPs in combination with low amounts of rNTPs.

When modified polymerase enzymes in accordance with the present invention are used in a suitable sequencing method, such as e.g. dye-primer sequencing, good DNA sequencing results are obtained with a dNTP concentration in the range of 50–500 $\mu$M of each dNTP. Preferably the DNTP concentration is between 100–300 $\mu$M. In these ranges the corresponding rNTP may be present at about the same concentration as the dNTP, or less. Preferably the rNTP is present at about 0.1 $\mu$M–100 $\mu$M, most preferable the rNTP is present at about 2.5 $\mu$M to 25 $\mu$M.

The concentration of rNTPs suitable for use with the present modified enzymes can be readily determined by titration and optimization experiments by those of ordinary skill in the art. The amount of rNTP or analogue needed will be affected by the type of experiment and may be influenced by the target size and purity as well as the choice of buffer and the particular species of enzyme.

The ratio of rNTP:dNTP will determine the frequency with which rNTPs are inserted into the growing oligonucleotide. Because hydrolysis will occur at each incorporated rNTP, the ratio of rNTP:dNTP can be adjusted to provide the user with flexibility to increase or decrease the size of the resulting fragments.

As is well understood, DNA is a polymer synthesized from dNTPs. Each deoxynucleoside triphosphate comprises a ribose sugar which contains a hydroxyl group at the 3' position and a hydrogen at the 2' position. Ribonucleotides also contain a hydroxyl group at the 3' portion of the sugar. However, rNTPs are distinguished from dNTPs at the 2' position of the sugar, where a second hydroxyl group replaces the hydrogen atom. In the present context, rNTPs exemplify the ability of the enzymes of the present invention to accurately incorporate 2' substituted nucleotides. However, the compounds of the invention are not limited to the use of unconventional nucleotides which are ribonucleotides. Modification of the thermostable polymerase sequence at the critical domain identified herein enables template directed incorporation of alternative 2' substituted nucleotides, such as 2'-hydroxyl, 3'-deoxy nucleotides and substituted 2'-fluoro or amino nucleotides.

As is described in the examples herein, the incorporation of 3'-deoxy, 2'-hydroxy ATP, referred to herein as cordycepin triphosphate, is facilitated by the presence of a second mutation in the thermostable polymerase which reduces discrimination against incorporation of a nucleotide containing a deoxy at the 3' position of the ribose. Such enzymes have been previously described for example in U.S. Ser. No. 08/448,223, filed May 23, 1995, which is incorporated herein by reference. ATCC Deposit No. 69820 provides the gene encoding a modified thermostable DNA polymerase of *Thermus aquaticus* that has reduced discrimination against incorporating analogues such as ddNTPs. Dideoxynucleotides have a substituted 3' position in comparison to conventional dNTPs. Thus, in combination with the present invention, the double mutation, exemplified herein by a E615G, F667Y mutant, provides means for utilizing nucleotide analogues which are substituted at the 3' and 2' positions of the ribose, in comparison to dNTPs (see Examples III and V).

A particular application of the invention is a rNTP sequencing method, wherein the sequencing primer is detectably labeled with a distinguishable fluorescent or radioactive tag. Unlike ddNTPs, incorporation of an unmodified rNTP does not result in a chain termination event. The DNA sequencing reaction comprising both rNTPs and dNTPs in combination with an enzyme of the invention, produces a mixture of randomly substituted primer extension products susceptible to cleavage at the 3'–5' phosphodiester linkage between a ribo- and an adjacent deoxyribonucleotide. Following primer extension in, for example, PCR amplification or cycle sequencing, and prior to resolving the primer extension products, by, for example, gel electrophoresis, the reaction mix is treated with either alkali, heat, a ribonuclease or other means for hydrolyzing the extension products at each occurrence of a ribonucleotide. For each labeled primer extension product, only the most 5' fragment, which is the immediate extension product of the labeled primer, is detectable on a sequencing gel. For a given target, analysis of the resulting sequencing gel provides a sequencing ladder, i.e., a series of identifiable signals in the G, A, T, and C, lanes corresponding to the nucleic acid sequence of the target. The resulting sequencing ladder provides the same information whether the method utilizes ddNTPs by conventional means, or rNTPs and the novel thermostable polymerases described herein. Thus, by use of the present invention, expensive ddNTPs are no longer required for DNA sequencing (see Example VI).

In an alternative sequencing method, chain-terminating ribonucleotides are employed. In this embodiment of the invention, 2'-hydroxy, 3'-deoxy nucleotides, such as cordycepin triphosphate, are utilized as terminators. These rNTP analogues can be fluorescently labeled and utilized for DNA sequencing. Lee et al. (supra.) have described the use of dye-terminator ddNTPs and U.S. Ser. No. 08/448,223 and EP Application 655,506, describe modified enzymes for use with ddNTPs. A thermostable DNA polymerase comprising both the modification present in AmpliTaq® DNA polymerase FS (see above) and that specified in Seq ID No. 1, wherein X is not glutamic acid (E), as described herein, can be used for efficiently incorporating the labeled rNTP analogues in a chain termination sequencing reaction. This process may be automated and does not require synthesis of dye labeled primers. Furthermore, because dye-terminator reactions allow all four reactions to be performed in the same tube, they are more convenient than dye-primer methods. The 2'-hydroxy, 3'-deoxy nucleotides can be synthesized from commercially available 3' nucleosides (3' dA, 3' dC, 3' dG and 3' dT Sigma Chemical Corporation, St. Louis, Mo.) and adding a 5' triphosphate as described in Ludwig, *Biophosphates and Their Synthesis Structure, Metabolism and Activity*, editors, Bruzik and Stec, Amsterdam, Elsevier Science Publishers, 1987, pages 201–204, which is incorporated herein by reference.

In addition to the utility of the enzymes of the present invention in novel sequencing methods, the modified enzymes described herein are useful in a number of molecular biology applications. In one embodiment, the modified enzyme is used in an amplification reaction mixture comprising both conventional and unconventional nucleotides, for example, dNTPs and at least one detectably labeled rNTP, the labels which include, for example, fluorescent labels or radioisotopes. Template directed synthesis of a complementary strand provides a DNA product containing ribonucleoside monophosphates at various positions along its length. Heat and/or alkali treatment hydrolyzes the nucleic acid extension product at each ribonucleotide. Thus, a family of DNA segments is provided wherein each fragment contains one label moiety at its 3' end. The size of the resulting nucleic acid fragments can be modified by adjusting the ratio and amount of rNTP included in the reaction.

The amplification of a target using rNTPs and the present enzymes provides numerous advantages depending upon the particular application. In the method described above using a labeled rNTP, the resulting family of fragments are all labeled with equal intensity: one label per oligonucleotide fragment. Procedures such as nucleic acid detection using an oligonucleotide probe array fixed to a silicon chip, optimally require that the amplified target is randomly fragmented within a fixed reproducible size range to limit formation of secondary structures for controlling hybridization kinetics. Further, for detecting hybridization to an array of thousands of probes on a chip, it may be preferable that the nucleic acid fragments are labeled with equal intensity. The present invention provides a means for producing families of fragments that meet this standard, and thereby facilitates the use of alternative detection formats such as the chip-based methods described by, for example, Cronin et al., 1996, *Human Mutation* 7:244–255, which is incorporated herein by reference.

In another embodiment, the use of one labeled primer and one unlabeled primer in an amplification reaction which comprises a thermostable polymerase of the invention and both rNTPs and dNTPs provides a means of simultaneously performing amplification and sequencing reactions. This method requires that four separate amplification reactions are conducted, one for each rNTP. Thus, for example, because the enzyme of the invention is suitable for target amplification by, for example, PCR, or other amplification means, the resulting product, if it is present, can be detected by conventional methods such as gel electrophoresis or probe hybridization using a portion of the reaction product. These detection methods will not result in hydrolysis of the incorporated ribonucleotides, and the RNA/DNA chimeric strands will behave as expected for a conventional nucleic acid amplification product. If a desired product is detected, a remaining portion of the same reaction mixture can be treated with alkali and analyzed by gel electrophoresis for nucleic acid sequence determination. Thus, following detection of the product, a subsequent sequencing reaction is unnecessary. This simplified procedure saves time and materials and provides increased accuracy by removing steps: the detected product is the sequenced product.

A similar procedure with four labeled rNTPs and one biotinylated primer could also be used. After amplification, the product is cleaved with alkali and the primer associated products are removed by reaction with strepavidin coated beads. The captured products are subsequently analyzed on a sequencing gel. This modification allows the sequencing reaction to be done in one tube, thus eliminating the need for four separate amplifications.

In another aspect of the invention, the enzymes described herein are useful for preparing RNA from a DNA template or for making substituted DNA for alkali mediated sterilization without the use of conventional sterilizing agents such as uracil-N-glycolsylase (UNG), as described in International Patent Publication No. WO 92/01814.

In an exemplified embodiment, the thermostable polymerase also contains a mutation in the 5'-3' exonuclease domain that serves to greatly attenuate this exonuclease activity. Modified forms of Taq polymerase are described in U.S. Pat. No. 5,466,591, which is incorporated herein by reference. In one embodiment of that invention, the codon encoding the glycine (G) residue at amino acid position 46 has been replaced with a codon encoding aspartic acid (D). The resulting enzyme has enhanced utility in cycle sequencing reactions due to the decreased 5'-3' exonuclease activity and is a preferred background for use with the present invention. The polymerase domain amino acid sequence and polymerase activity are unaffected by the presence of the (G46D) mutant in comparison to the wild-type enzyme.

In a commercial embodiment of the invention, kits for practicing methods that are improved by use of the present invention are an aspect of the invention. Kits may include, for example, a novel thermostable polymerase of the invention, and may additionally include reagents for DNA sequencing such as rNTPs, dNTPs, and appropriate buffers. Where rNTPs are unlabeled, a labeled primer may be included.

The following examples are offered by way of illustration only and are by no means intended to limit the scope of the claimed invention.

EXAMPLE I

Expression of a Modified Taq Polymerase Gene Having Reduced Discrimination Against Unconventional Nucleotides The C-terminal amino acid portion of Taq DNA polymerase encodes the polymerase active site domain (Lawyer et al., 1993, *PCR Methods and Applications* 2:275–287, which is incorporated herein by reference). A DNA fragment containing this region was isolated from the full-length Taq gene and mutagenized by PCR amplification in the presence of manganese (Leung et al., 1989, *Technique* 1(1): 11–15). For this example, all restriction enzymes were purchased from New England Biolabs, Beverly, Mass. The mutagenized fragments were digested with PstI and BglII and cloned into a Taq expression plasmid, pLK102, which had been digested with PstI and BglII. Plasmid pLK102 is a modified form of Taq expression plasmid pSYC1578 (Lawyer et al., supra.). The HincII/EcoRV fragment located 3' to the polymerase coding region was deleted to create plasmid pLK101. A 898 base pair PstI-BglII fragment was subsequently deleted from pLK101 and replaced by a short PstI-EcoRV-BglII oligonucleotide duplex to create plasmid pLK102. Thus, this deletion removes 900 base pair from the 3' end of the Taq DNA pol gene and replaces it with a short piece of DNA.

The resulting expression plasmids were transformed into *E. coli* strain N1624 (*E. coli* Genetic Stock Center at Yale University, strain No. CGSC #5066) and the resulting transformants were screened for the ability to efficiently incorporate rNTPs in comparison to the wild-type enzyme. Using this procedure, mutant C1 was identified as having the ability to more efficiently incorporate rNTPs.

To determine which portion of the Taq polymerase gene was responsible for the altered phenotype, the mutagenized Taq expression plasmid (pC1), isolated from mutant C1, was digested with various restriction enzymes and the resulting restriction fragments were subcloned into the wild-type Taq DNA polymerase gene of pLK101, replacing the unmutgenized restriction fragments. Analysis of the resulting subclones indicated that the mutation responsible for the phenotype was contained within a 265 base pair NheI to BamHI restriction fragment.

DNA sequence analysis was performed on this region of pC1 using the ABI PRISM$^a$ Dye Terminator Cycle Sequencing Core Kit with AmpliTaq® DNA polymerase FS from Applied Biosystems, Foster City, Calif., and the Applied Biosystems Model 373A DNA Sequencing System. The sequence analysis identified two missense mutations in the Taq polymerase gene between the NheI and BamHI sites. A mutation at amino acid position 615 caused a Glutamic acid residue (E) to be replaced by a Glycine residue (G) and another mutation at position 653 replaced an Alanine (A) residue with a Threonine (T). Numbering is initiated at the codon encoding the first methionine residue of the mature protein, as in U.S. Pat. No. 5,079,352. The E615G mutation was caused by a GAG to GGG change in codon 615. The A653T mutation was caused by a GCC to ACC change at codon 653. Plasmid C1 in *E. coli* host strain N1624 was deposited with the ATCC on Jul. 17, 1996, and given accession No. 98107.

The two point mutations were separately analyzed by subcloning each separately into a wild-type Taq polymerase gene, using recombinant PCR (Innis et al. editors, *PCR Protocols*, San Diego, Academic Press, 1990, Chapter 22, Entitled "Recombinant PCR", Higuchi, pages 177–183). The resulting expression products were analyzed to determine whether E615G or A653T or both mutations were responsible for the ribonucleotide incorporation phenotype. The results of this experiment indicated that the E615G mutation was solely responsible for the mutant phenotype.

For further analysis and quantitation of the incorporation efficiency of nucleotide analogs, the 265 base pair BamHI-NheI PCR fragment containing E615G was cloned into a Taq expression vector, pRDA3-2. Expression vector pRDA3-2 contains the full-length Taq gene operably linked to the phage lambda PL promoter. The exonuclease domain of the Taq gene in this vector contains a point mutation at the codon encoding glycine, amino acid residue 46, that reduces 5'-3' exonuclease activity. However, the gene sequence within the polymerase domain of the expression vector pRDA3-2 is identical to the wild-type Taq gene sequence. Plasmid RDA3-2 is fully described in U.S. Pat. No. 5,466,591, which is incorporated herein by reference, wherein the plasmid is referred to as "clone 3-2." Plasmid pRDA3-2 was digested with BamHI and NheI and the 265 base pair PCR fragment was ligated into the vector by conventional means.

The resulting plasmid, pLK108, was transformed into *E. coli* strain DG116 (ATCC No. 53606). This plasmid encodes a thermostable DNA polymerase herein referred to as G46D, E615G Taq. A mutant, G46D, E615G, F667Y Taq, was created by combining the E615G and F667Y mutations by recombinant PCR into a BamHI-NheI fragment. This fragment was cloned into plasmid pRDA3-2 to create plasmid pLK109. The expressed thermostable DNA polymerase protein from plasmids pLK108 and pLK109 were purified according to the method described by Lawyer et al., supra., although the chromatography steps were omitted. The sequence of the inserts was confirmed by DNA sequence analysis. An additional mutation in the sequence was detected in the pLK108 insert; however, this mutation does not change the amino acid sequence of the protein.

Following partial purification, the activity of the modified enzyme was determined by the activity assay described in Lawyer et al., 1989, *J. Biol. Chem.* 264:6427–6437, which is incorporated herein by reference. The activity of the modified enzyme was calculated as follows: one unit of enzyme corresponds to 10 nmoles of product synthesized in 30 minutes. DNA polymerase activity of the wild-type enzyme is linearly proportional to enzyme concentration up to 80–100 pmoles dCMP incorporated (diluted enzyme at 0.12–0.15 units per reaction). Activity of the E615G, G46D and E615G, F667Y, G46D mutants is linearly proportional to enzyme concentrations up to 0.25–3 pmoles dCMP incorporated (diluted enzyme at $6 \times 10^{-4}$ to $5 \times 10^{-3}$ units per reaction). This enzyme preparation was utilized in the incorporation and sequencing reactions described in Examples III–V. For Examples II and VI, enzyme was purified as described in Lawyer et al. (supra.).

EXAMPLE II

Assay to Compare Efficiency of Incorporation

The relative ability G46D and G46D, E615G Taq to incorporate rNTPs was determined by measuring the amount of $[\alpha\text{-}^{32}P]$rNTP each enzyme could incorporate at limiting enzyme concentration into an activated salmon sperm DNA template. To measure the incorporation of rATP, a reaction mixture was prepared so that the final concentrations in a 50 µl reaction were: 12.5 µg activated salmon sperm DNA, prepared as described below, 200 µM each dCTP, dGTP and dTTP (Perkin Elmer, Norwalk, Conn.), 100 µM $[\alpha\text{-}^{32}P]$rATP, 1 mM β-mercaptoethanol, 25 mM N-tris[hydroxmethyl]methyl-3-amino-propanesulfonic acid (TAPS) pH 9.5, 20° C., 50 mM KCl and 2.25 MM MgCl$_2$.

Similar assay mixtures were prepared to measure the incorporation of rCTP, rGTP and rUTP. In each case, the rNTP was radiolabeled and present at 100 µM and the three remaining dNTPs (dATP, dGTP and dTTP for rCTP, DATP, dCTP and dTTP for rGTP and DATP, dCTP and dGTP for rUTP) were present at 200 µM each. As a standard, incorporation of the corresponding $[\alpha\text{-}^{32}P]$dNTP by each enzyme was also measured. The assay mixture for these assays was similar to the rNTP incorporation assay above except that each $[\alpha\text{-}^{32}P]$rNTP was replaced with 100 µM of the corresponding $[\alpha\text{-}^{32}P]$DNTP. Crude salmon sperm DNA, 1 g/l, from Worthington Biochemical, (Freehold, N.J.) was activated by incubation in 10 mM Tris-HCl, pH 7.2, 5 mM MgCl$_2$, at 2° C.–8° C. for 96 hours. EDTA and NaCl were then added to 12.5 mM and 0.1M, respectively. The DNA was then extracted with phenol chloroform and then ethanol precipitated and resuspended in 10 mM Tris, 1 mM EDTA, pH 7.5. The activated DNA preparation was then dialyzed against the same buffer.

Forty-five microliters of each reaction mixture were aliquoted into five 0.5 ml eppendorf tubes for each of the 5'-labeled nucleotide precursors. Thus, each of G46D Taq and G46D, E615G Taq were assayed in duplicate with one tube remaining for a negative control. The polymerization reaction in two tubes of each assay mix was initiated with 5 µl of either G46D Taq polymerase (0.02 units) or G46D, E615G Taq (0.002 units). As a control for the level of background, 5 µl of enzyme dilution buffer rather than enzyme was added to the negative control reaction.

Each reaction was vortexed briefly and incubated 10 minutes 75° C. The reactions were stopped by addition of 10 µl 60 mM EDTA and stored on ice. For each sample, 50 µaliquots of the 60 µl reaction were diluted with 1 ml 2 mM EDTA, 50 µg/ml sheared salmon sperm DNA. The DNA was precipitated with TCA using standard procedures and collected on GF/C filter discs (Whatman, Kent, England). The amount of incorporated $[\alpha\text{-}^{32}P]$ labeled nucleotide or ribonucleotide was quantitated by liquid scintillation spectrometry and the number of pmoles incorporated was then calculated. The number of pmoles of each rNTP incorporated by each enzyme was normalized to the number of pmoles of the corresponding $[\alpha\text{-}^{32}P]$dNTP incorporated by each enzyme. The resulting data is shown below.

Incorporation Ratio of rNTP to dNTP for G46D and G46D, E615G Taq

| Enzyme | pMoles Incorporated (percent) | | | | | | | |
|---|---|---|---|---|---|---|---|---|
| | dATP | rATP | dCTP | rCTP | dGTP | rGTP | dTTP | rUTP |
| G46D | 27.74 | 0.052 | 34.6 | 0.76 | 36.94 | 0.133 | 28.79 | 0 |
| | (100%) | (0.18%) | (100%) | (0.22%) | (100%) | (0.36%) | (100%) | (0) |
| G46D, E615G | 0.67 | 1.41 | 2.82 | 5.33 | 3.27 | 5.96 | 0.688 | 0.545 |
| | (100%) | (210%) | (100%) | (189%) | (100%) | (181%) | (100%) | (79%) |

These results indicate that G46D, E615G incorporates ribonucleotides more than 500-fold more efficiently than can G46D. Thus, a missense mutation in the polymerase gene at codon 615, provided a novel phenotype: a thermostable DNA polymerase capable of efficiently incorporating ribonucleotides in addition to deoxyribonucleotides.

EXAMPLE III

Assay to Compare Efficiency of Incorporation of 3'deoxy ATP (Cordycepin)

The relative ability G46D; G46D, E615G; G46D, E615G, F667Y and G46D, F667Y Taq to incorporate 3'-deoxy adenosine 5'-triphosphate (cordycepin triphosphate) was determined by measuring the amount of [α-$^{32}$P]cordycepin triphosphate each enzyme could incorporate at limiting enzyme concentration into an activated salmon sperm DNA template. To measure the incorporation of [α-$^{32}$P] cordycepin triphosphate, the assay was composed so that the final concentrations in a 50 μl reaction were: 12.5 μg activated salmon sperm DNA, 200 μM each dCTP, dGTP and dTTP, 50 μM dATP (Perkin Elmer), 50 μM [α-$^{32}$P] 3'dATP/3' dATP (New England Nuclear, Sigma), 1 mM β-mercaptoethanol, 25 mM N-tris[hydroxmethyl]methyl-3-amino-propanesulfonic acid (TAPS) pH 9.5, 20° C., 55 mM KCl and 2.25 mM MgCl$_2$.

Forty-five microliters of each reaction mixture were aliquoted into nine 0.5 ml eppendorf tubes, thus each reaction will be done with either G46D; G46D, E615G; G46D, E615G, F667Y or G46D, F667Y Taq in duplicate with one tube remaining for a no enzyme control. The polymerization reaction in two tubes of assay mix was started with 5 μl (0.058 units) of G46D Taq polymerase. The same was done for G46D, E615G Taq (0.0025 units), G46D, E615G, F667Y Taq (0.0034 units) or G46D, F667Y Taq (0.083 units). As a control for the level of background, the one remaining tube was started with enzyme dilution buffer rather than enzyme.

Each reaction was vortexed briefly and incubated for 10 minutes at 75° C. The reactions were stopped by addition of 10 μl 60 mM EDTA and stored on ice. For each sample, 50 μl aliquots of the 60 μl reaction were diluted with 1 ml 2 mM EDTA, 50 μg/ml sheared salmon sperm DNA. The DNA was precipitated with TCA using standard procedures and collected on GF/C filter discs (Whatman, Kent, England). The amount of incorporated [α-$^{32}$P] labeled nucleotide was quantitated by liquid scintillation spectrometry and the number of pmoles incorporated was then calculated. The number of pmoles of [α-$^{32}$P]cordycepin triphosphate incorporated by each enzyme was divided by the number of units of each enzyme used in the assay to give the pmoles incorporated per unit enzyme. A chart of this data is shown below.

Incorporation of [α-$^{32}$P]cordycepin by G46D; G46D, E615G; G46D, E615G, F667Y and G46D, F667Y Taq

| Enzyme | pmoles Incorporated per unit of Enzyme |
| --- | --- |
| G46D | 0.221 |
| G46D, E615G | 1.56 |
| G46D, E615G, F667Y | 893.6 |
| G46D, F667Y | 0.74 |

These results indicate that both the E615G and the F667Y mutations are required for the efficient incorporation of the cordycepin molecule into DNA.

EXAMPLE IV

Alkaline Cleavage DNA Sequencing Using G46D, E615G Taq DNA Polymerase

This example demonstrates the application of the modified polymerase of the invention to alkaline cleavage sequencing, utilizing partially rNTP substituted DNA. The ratio of rNTP to DNTP in the reaction mixes was between 1:80 and 1:8. Primer extension reactions were performed in a buffer consisting of 50 mM Bicine (pH 8.3), 25 mM KOAc, and 2.5 mM MgCl$_2$. Four individual reactions, one for each of the four rNTPs, were performed. Each reaction (50 μl) contained 200 μM each DATP, dCTP, dGTP and dTTP (Perkin-Elmer) and 0.09 pmoles M13mp18 single-strand DNA template (Perkin-Elmer) annealed to 5'-[$^{32}$P] labeled DG48 (Lawyer et al., 1993, *PCR Methods and Applications* 2:275–287). The reactions also contained 2.5, 2.5, 2.5 or 25 μM rATP, rCTP, rGTP or rUTP, respectively.

Each of the four reactions was initiated by addition of 7 units of G46D E615G Taq DNA polymerase and incubated at 75° C. for 10 minutes. The reactions were stopped by addition of 10 μl 60 mM EDTA and placed on ice. Twenty μl of each reaction were added to 80 μl of 50 mM Bicine (pH 8.3), 25 mM KOAc, and 2.5 mM MgCl$_2$. Cleavage products were produced by addition of 7 μl of 1N NaOH and incubation for 15 minutes at 98° C. The reactions were neutralized by addition of 7 μl of 1N HCl. Each reaction was precipitated by the addition of 312 μl 95% ethanol and 10 μl 3M sodium acetate (pH 4.8). The reactions were microcentrifuged for 15 minutes to collect precipitate, the supernatant was removed, the pellets were washed with 500 μl 70% ethanol and dried. Each pellet was resuspended in 5 μl of 0.5X Stop Buffer (available from Perkin Elmer, Norwalk, Conn.; contains 95% formamide, 20 mM EDTA and 0.05% bromphenol blue), heated at 98° C. for 3 minutes, and directly loaded onto a pre-electrophoresed 6% polyacrylamide/8M urea DNA sequencing gel and electrophoresed. The gel was dried and exposed to X-ray film. The resulting film revealed a clear sequencing ladder which provided in excess of 100 bases of correct sequence.

EXAMPLE V

DNA Sequencing Using G46D, E615G, F667Y Taq DNA Polymerase and 3' deoxy Nucleotide Triphosphates This example demonstrates the application of the modified polymerase, G46D, E615G, F667Y Taq to DNA sequencing using 3'deoxy nucleotide triphosphates. This experiment was performed using 3'deoxy ATP; however, it could be extended to use with the other 3'deoxy nucleotides as well. Primer extension reactions were performed in a buffer consisting of 50 mM Bicine (pH 8.3), 25 mM KOAc, and 2.5 mM MgCl$_2$. Each reaction (50 μl) contained 200 μM each dATP, dCTP, dGTP and dTTP (Perkin-Elmer) and 0.09 pmoles M13mp18 single-strand DNA template (Perkin-Elmer) annealed to 5'-[$^{32}$P] labeled DG48. The reactions also contained 0, 0.1, 0.25, 0.5, 1, or 5 μM 3'deoxy ATP.

Each of the reactions was initiated by addition of 7 units of G46D, E615G, F667Y Taq DNA polymerase and incubated at 75° C. for 10 minutes. The reactions were stopped by addition of 10 μl 60 mM EDTA and placed on ice. Thirty μl of each reaction was ethanol precipitated and resuspended in Stop Buffer, heated at 98° C. for 3 minutes, and directly loaded onto a pre-electrophoresed 6% polyacrylamide/8M urea DNA sequencing gel and electrophoresed. The gel was dried and exposed to X-ray film. The lanes which contained reactions done in the presence of cordycepin contained clearly discernible termination ladders. The lanes containing the most cordycepin, i.e., 5 μM, showed a termination ladder in which, on average, the bands were shorter in length than the lanes in which the cordycepin levels were lower. The lane containing the reaction done in the absence of cordycepin, showed mostly full-length product and no termination ladder. These results indicate that the mutant enzyme is able to incorporate cordycepin and incorporation of this molecule into a primer extension product causes

23 termination. This method could also be used to create a DNA sequencing ladder, with 3'deoxy CTP, 3'deoxy GTP and 3'deoxy UTP as well.

EXAMPLE VI

Dye Primer PCR Sequencing with G46D E615G Taq DNA Polymerase

This example demonstrates the application of the modified polymerase of the invention to dye primer sequencing, utilizing ribonucleoside triphosphates (rNTPs) in PCR and a ratio of rNTP:dNTP of no more than 1:30. Four individual reactions, one for each of the rNTPs, were performed. PCR sequencing reactions were performed in a buffer consisting of 25 mM Tris-HCl (pH 9), 5.0 mM $MgCl_2$, and 10% glycerol (v/v). Each reaction also contained 500 μM each dATP, dCTP, dGTP, dTTP (Perkin Elmer), $5 \times 10^6$ copy/μl pBSM13+ plasmid (Strategene) template linearized with XmnI restriction endonuclease, and 0.05 unit/μl G46D E615G Taq DNA polymerase. Ribo-ATP reactions (10 μl) contained 2.5 μM rATP (Pharmacia Biotech), 0.1 μM JOE M13 Reverse Dye Primer (Perkin Elmer), and 0.1 μM primer ASC46 (5'-CGCCATTCGCCATTCAG), (Seq ID No.7). Ribo-CTP reactions (10 μl) contained 2.5 μM CTP (Pharmacia Biotech), 0.1 μM FAM M13 Reverse Dye Primer (Perkin Elmer), and 0.1 μM primer ASC46. Ribo-GTP reactions (20 μl) contained 2.5 μM rGTP (Pharmacia Biotech), 0.1 μM TAMRA M13 Reverse Dye Primer (Perkin Elmer), and 0.1 μM primer ASC46. Ribo-UTP reactions (20 μl) contained 16 μM rUTP (Pharmacia Biotech), 0.1 μM ROX M13 Reverse Dye Primer (Perkin Elmer), and 0.1 μM primer ASC46.

Each of the four reactions were placed in a preheated (75° C.) Perkin Elmer GeneAmp® PCR System 9600 thermal cycler and subjected to 30 cycles of 95° C. for 10 seconds, 55° C. for 10 seconds, 1 minute ramp to 65° C., and 65° C. for 5 minutes. The rATP and rCTP reactions each generated $6 \times 10^{11}$ copies of dye-labeled amplified 300 base pair product, and the rGTP and rUTP reactions each generated $1.2 \times 10^{12}$ copies of dye-labeled amplified 300 base pair product.

To determine the DNA sequence of the amplified PCR products without requiring a separate enzymatic DNA sequencing reaction, the reactions were pooled, treated with base and heat, neutralized, and precipitated as follows. Four μl each of the rATP and rCTP reactions and 8 μl each of the rGTP and rUTP reactions were pooled. Two microliters of 0.25 M EDTA (pH 8.0) (10 mM final), 10 μl 1 M NaOH (200 mM final), and 14 μl $H_2O$ were added to the pooled reaction which was then incubated at 95° C. for 5 minutes in a GeneAmp® PCR System 9600 thermal cycler and neutralized with 10 μl 1M HCl. The pooled reaction was then precipitated by the addition of 150 μl 95% ethanol followed by an incubation at 4° C. for 15 minutes. It was then microcentrifuged for 15 minutes at 4° C. to collect the precipitate, and the supernatant removed by aspiration. The pellet was washed with 300 μl 70% ethanol, microcentrifuged for 5 minutes, the supernatant removed by aspiration, and the pellet dried. The pellet was resuspended in 6 μl formamide:50 mg/ml Blue dextran (in 25 mM EDTA) 5:1 (v/v) and heated at 90° C. for 3 minutes. One and a half μl of the resuspended pellet was directly loaded onto a pre-electrophoresed 5% Long Ranger (FMC BioProducts), 6M urea sequencing gel. It was then electrophoresed and analyzed on a Perkin Elmer ABI Prism™ 377 DNA Sequencer according to the manufacturers instructions. Automated base-calling by the Perkin Elmer ABI Prism™ Sequencing Analysis software resulted in greater than 99% accuracy for DNA sequence determination of the PCR amplified 300 base pair product.

EXAMPLE VII

Construction of Novel Chimeric Ribonucleotide Incorporating Thermostable DNA Polymerases The construction of plasmids pTMA25 and pTMA30 are described in Example I of patent application, attorney docket number 1043P, entitled "Mutant Chimeric DNA Polymerase," which was filed on Jul. 9, 1997, and is incorporated herein by reference. Plasmids pTMA25 and pTMA30 encode, respectively, proofreading and non-proofreading versions of novel chimeric thermostable DNA polymerases comprising a portion of the amino terminal or 5'-nuclease domain of *Thermus aquaticus* (Taq) DNA Polymerase fused to the remainder of the 5'-nuclease domain and all of the polymerase domain of *Thermotoga maritima* (Tma) DNA Polymerase. Specifically, the Taq domain encodes amino acids 1 through 190 of Taq DNA Polymerase, and, in addition, contains a mutation at codon 46 which changes glycine to aspartic acid (G46D) to eliminate the 5'-nuclease domain. See issued U.S. Pat. No. 5,466,591, incorporated herein by reference. The Tma domain encodes amino acids 191 through 893 of Tma DNA Polymerase. See U.S. Pat. Nos. 5,420,029 and 5,624,833, incorporated herein by reference. To eliminate the 3'–5' exonuclease or "proof-reading" activity in the Tma domain, pTMA30 contains mutations at codons Tma 323 and 325 which change D323 to alanine and E325 to alanine (D323A and E325A) as described in Example I of the above referenced application, attorney docket number 1043P.

The Tma coding portion of plasmids pTMA25 and pTMA30 encodes the S Q I E L R I (Seq. ID No. 4) motif with glutamic acid corresponding to position 678, as indicated in Table 1. To change the pTMA25 and pTMA30 coding sequences at amino acid position 678, oligonucleotides FR624, 5'-GTGGATCGTC TCCGCGGACT ACTC-CCAAAT AGGCCTACGT ATCCTCGCCC ATCTCA, (Seq ID No. 8) and FR625, 5'-ATGGGCGAGG ATACGTAGGC CTATTTGGGA GTAGTCCGCG GAGACGATCC ACCAGT, (Seq ID No. 9) were annealed and ligated with BstXI (New England Biolabs)-digested pTMA25 or pTMA30 plasmid DNAs, at a 3:1 molar ratio of FR624/625 duplex: digested pTMA25 or pTMA30 vector, respectively. The ligated DNAs were transformed into *E. coli* K-12 strain DG116 and ampicillin resistant transformants screened by restriction enzyme digestion for the desired 8.2 kb plasmid. Replacement of the wild-type Tma DNA sequence, which is flanked by BstXI sites, with the annealed FR624/FR625 duplex DNA fragment results in the elimination of one of the four BamHI sites in pTMA25 or pTMA30 and acquisition of SacI, StuI and SnaBI sites. Candidate clones were confirmed by DNA sequence analysis and one of the correct desired plasmids derived from pTMA25 was designated E678G pTMA25, while one of the correct desired plasmids derived from pTMA30 was designated E678G pTMA30.

EXAMPLE VIII

Expression and Purification of E678G Tma25 DNA Polymerase and E678G Tma30 DNA Polymerase Fresh overnight cultures at 30° C. of *E. coli* K-12 strains E678G pTMA25/DG116 and E678G pTMA30/DG116 in glucose (0.2%), thiamine (10 pg/ml) and casamino acids (0.25%) ampicillin-containing (100 μg/ml) minimal media were diluted to 1% (v/v) into 500 ml fresh media and grown with shaking at 30° C. in a fembach flask to an $A_{680}$ of 0.68. The flasks were placed in a 39° C. shaker box and induced cells were harvested by centrifugation the next morning. Cell pellets were stored at −20° C.

Cell pellets (ca. 2 ml) were thawed in a conical 15 ml tube with 2 ml 100 mM Tris-Cl, pH7.5, 20 mM EDTA, 2 mM DTT and disrupted by sonication on ice (45 seconds with 1 minute cooling, repeated 3 times). The cell lysates were diluted to 10 ml with 50 mM Tris-Cl, pH7.5, 10 mM EDTA, 1 mM DTT (ca. 30 mg protein/ml), adjusted to 0.2M $(NH_4)_2SO_4$ with 4.0M ammonium sulfate, heated to 75° C. for 15 min. to denature host proteins, cooled on ice for 15 min., and centrifuged at 10,000×G at 4° C. for 10 min. to precipitate denatured E. coli host proteins. Bulk nucleic acid was precipitated from the soluble heat-treated extract proteins following addition of polyethyleneimine to 0.6%, standing on ice for 15 min. and centrifuging at 10,000×G for 10 min. Ammonium sulfate was added to the recovered supernatants to increase the concentration of ammonium sulfate to 0.3M, and the protein samples applied at 4° C. to 2.0 ml Phenyl Sepharose 6 Fast Flow (Pharmacia, Piscataway, N.J.) columns that had been equilibrated with 50 mM Tris-Cl, pH7.5, 0.3M $(NH_4)_2SO_4$, 10 mM EDTA, 1 mM DTT. The columns were then serially washed with three column volumes each (6 ml) 50 mM Tris-Cl, pH7.5, 0.3M $(NH_4)_2SO_4$, 10 mM EDTA, 1 mM DTT; 25 mM Tris-Cl, pH 7.5, 1 mM EDTA, 1 mM DTT; 25 mM Tris-Cl, pH 7.5, 1 mM EDTA, 1 mM DTT, 20% (v/v) ethylene glycol. The novel chimeric E678G Tma25 and E678G Tma30 DNA Polymerases were step-eluted from the phenyl sepharaose columns with 6 ml of 25 mM Tris-Cl, pH 7.5, 1 mM EDTA, 1 mM DTT, 20% (v/v) ethylene glycol, 2.0M urea. The two DNA polymerase preparations were then each applied at 4° C. to a 1 ml Heparin Sepharose (Pharmacia) column that had been equilibrated with 25 mM Tris-Cl, pH 7.5, 1 mM EDTA, 1 mM DTT, 50 mM KCl. The columns were serially washed with 3 column volumes of the same equilibration buffer and then with three column volumes of 25 mM Tris-Cl, pH 7.5, 1 mM EDTA, 1 mM DTT, 100 mM KCl. The DNA polymerases were step-eluted from the heparin sepharose columns with 3 ml of 25 mM Tris-Cl, pH 7.5, 1 mM EDTA, 1 mM DTT, 400 mM KCl. Peak activity containing fractions were pooled and concentrated on Ultrafree-15 centrifugal filter devices (Millipore Corp., Bedford, Mass.) according to the manufacturer's instructions. The concentrated DNA polymerase preparations were dialyzed extensively at 4° C. against 60 mM Tris-Cl, pH8.0, 300 mM KCl, 3 mM DTT, 0.3 mM EDTA. The dialyzed novel chimeric E678G Tma25 and E678G Tma30 DNA Polymerase samples were diluted three-fold with 80% (v/v) autoclaved glycerol, 10% (v/v) Tween 20 (Pierce) and water to provide storage stable preparations of the novel chimeric E678G Tma25 and E678G Tma30 DNA Polymerases in 20 mM Tris-Cl, pH 8.0, 100 mM KCl, 1 mM DTT, 0.1 mM EDTA, 0.2% Tween 20 and 50% glycerol.

EXAMPLE IX

Assay to Compare Efficiency of Incorporation

The ability of E678G Tma mutant enzymes to incorporate rNTPs was determined by measuring the amount of $[\alpha-^{33}P]$ rNTP that could be incorporated and compared with the amount of $[\alpha-^{33}P]$rNTP that a F730Y Tma mutant enzyme could incorporate at limiting enzyme concentration into an activated salmon sperm DNA template. In Tma, the mutation F730Y corresponds to the F667Y mutation in Taq polymerase. As described herein, this mutation effects dideoxynucleotide incorporation.

To measure the incorporation of rATP, a reaction mixture was prepared so that the final concentrations in a 50 μl reaction were: 29.3 μg activated salmon sperm DNA, prepared as described below, 200 μM each dCTP, dGTP and dTTP (Perkin Elmer, Norwalk, Conn.), 100 μM $[\alpha-^{33}P]$ rATP, 1 mM β-mercaptoethanol, 25 mM Tris-Cl pH 8.8, 20° C., 50 mM KCl and 1.25 mM $MgCl_2$.

Similar assay mixtures were prepared to measure the incorporation of rCTP, rGTP and rUTP. In each case, the rNTP was radiolabeled and present at 100 μM and the three remaining dNTPs (dATP, dGTP and dTTP for rCTP, dATP, dCTP and dTTP for rGTP and dATP, dCTP and dGTP for rUTP) were present at 200 μM each. As a standard, incorporation of the corresponding $[\alpha-^{33}P]$dNTP by each enzyme was also measured. The assay mixture for these assays was similar to the rNTP incorporation assay above except that each $[\alpha-^{33}P]$rNTP was replaced with 100 μM of the corresponding $[\alpha-^{33}P]$dNTP. Activated salmon sperm DNA, 1 g/l, from Worthington Biochemical, (Freehold, N.J.) was prepared by incubation with 1.0 unit DNAse I per mg salmon sperm DNA at 24° C. for 10–12 min. in 50 mM Tris-Cl, pH 7.5, 5 mM $MgCl_2$. EDTA was added to 12.5 mM. The DNA was then extracted with phenol chloroform and then ethanol precipitated and resuspended in 10 mM Tris-Cl, 1 mM EDTA, pH 7.5. The activated DNA preparation was then dialyzed against the same buffer.

Forty-five microliters of each reaction mixture were aliquoted into five 0.5 ml eppendorf tubes for each of the 5'-labeled nucleotide precursors. Thus, each of F730Y Tma30 and E678G Tma30 DNA Polymerases were assayed in duplicate with one tube remaining for a negative control. In addition, the ability of E678G Tma25 DNA Polymerase to incorporate ribonucleotides and deoxynucleotides was compared for a representative purine nucleotide (guanine) and a representative pyrimidine nucleotide (uracil/thymine) The polymerization reaction in two tubes of each assay mix was initiated with 5 μl of either F730Y Tma30 polymerase (0.1 units), or E678G Tma30 (0.04 units), or E678G Tma25 (0.04 units). As a control for the level of background, 5 μl of enzyme dilution buffer rather than enzyme was added to the negative control reaction.

Each reaction was vortexed briefly and incubated 10 minutes 75° C. The reactions were stopped by addition of 10 μl 60 mM EDTA and stored on ice. For each sample, 50 μl aliquots of the 60 μl reaction were diluted with 1 ml of 2 mM EDTA, 50 μg/ml sheared salmon sperm DNA. The DNA was precipitated with TCA using standard procedures and collected on GF/C filter discs (Whatman, Kent, England). The amount of incorporated $[\alpha-^{33}P]$ labeled nucleotide or ribonucleotide was quantitated by liquid scintillation spectrometry and the number of pmoles incorporated was then calculated. The number of pmoles of each rNTP incorporated by each enzyme was normalized to the number of pmoles of the corresponding $[\alpha-^{33}P]$dNTP incorporated by each enzyme. The resulting data is shown below.

Incorporation of rNTP or dNTP for Tma vs. E678G
Tma Enzymes

| | pMoles Incorporated (percent) | | | | | | | |
|---|---|---|---|---|---|---|---|---|
| Enzyme | dATP | rATP | dCTP | rCTP | dGTP | rGTP | dTTP | rUTP |
| F730Y Tma30 | 102.8 (100%) | 0.02 (<0.1%) | 93.4 (100%) | 0.1 (<0.2%) | 106.8 (100%) | 0.6 (<0.5%) | 78.3 (100%) | 0 (<0.1%) |
| E678G Tma30 | 45 (100%) | 41.1 (91.3%) | 40.3 (100%) | 42.6 (106%) | 49.5 (100%) | 51.9 (105%) | 38.9 (100%) | 32.4 (83.3%) |
| E678G Tma25 | | | | | 49.0 (100%) | 52.2 (107%) | 38.7 (100%) | 31.3 (81%) |

These results indicate that the novel DNA polymerases of the invention, for example, E678G TMA30 and E678G TMA25 DNA Polymerases, incorporate ribonucleotides 200-fold to greater than 1,000-fold more efficiently than previously described thermostable DNA polymerases. Thus, a missense mutation in the Tma DNA polymerase gene at codon 678, provided a novel phenotype: a thermostable DNA polymerase capable of efficiently incorporating ribonucleotides in addition to deoxyribonucleotides.

EXAMPLE X

Dye Primer PCR Sequencing with E678G Tma25 and E678G Tma30 DNA Polymerases

This example demonstrates the application of the novel polymerases of the invention to dye primer sequencing, utilizing ribonucleoside triphosphates (rNTPs) in PCR and a ratio of rNTP:dNTP of no more than 1:30. Four individual reactions, one for each of the rNTPs, were performed. PCR sequencing reactions were performed in a buffer consisting of 25 mM Tris-HCl (pH 8.8), 50 mM KCl, 3.0 mM $MgCl_2$, and 5% glycerol (v/v). Each reaction also contained 200 $\mu$M each dATP, dCTP, dTTP (Perkin Elmer), $c^7$dGTP, (Pharmacia), $5 \times 10^6$ copy/$\mu$l pBSM13$^+$ plasmid (Stratagene) template linearized with XmnI restriction endonuclease, and 0.02 unit/$\mu$l E678G Tma25 DNA Polymerase or 0.16 unit/$\mu$l E678G Tma30 DNA Polymerase, respectively. Ribo-ATP reactions (5 $\mu$l) contained 2.0 $\mu$M rATP (Pharmacia Biotech), 0.08 $\mu$M JOE M13 Reverse Dye Primer (Perkin Elmer), and 0.1 $\mu$M primer ASC45 (5'-GAAAGGAGCGGGCGCTA G), (Seq ID No. 10). Ribo-CTP reactions (5 $\mu$l) contained 2.0 $\mu$M rCTP (Pharmacia Biotech), 0.08 $\mu$M FAM M13 Reverse Dye Primer (Perkin Elmer), and 0.1 $\mu$M primer ASC45. Ribo-GTP reactions (10 $\mu$l) contained 1.2 $\mu$M rGTP (Pharmacia Biotech), 0.08 $\mu$M TAMRA M13 Reverse Dye Primer (Perkin Elmer), and 0.1 $\mu$M primer ASC45. Ribo-UTP reactions (10 $\mu$l) contained 7.0 $\mu$M rUTP (Pharmacia Biotech), 0.08 $\mu$M ROX M13 Reverse Dye Primer (Perkin Elmer), and 0.1 $\mu$M primer ASC45.

Each of the four reactions were placed in a preheated (95° C., 45 sec) Perkin Elmer GeneAmp® PCR System 9600 thermal cycler and subjected to 35 cycles of 95° C. for 15 seconds, 55° C. for 15 seconds, 1 minute ramp to 70° C., and 70° C. for 1 minute, with a final, last cycle extension at 70° C. for 5 min. The rATP and rCTP reactions each generated $2.4 \times 10^{11}$ copies of dye-labeled amplified 398 base pair product, and the rGTP and rUTP reactions each generated $4.8 \times 10^{11}$ copies of dye-labeled amplified 398 base pair product.

To determine the DNA sequence of the amplified PCR products without requiring a separate enzymatic DNA sequencing reaction, the reactions were pooled, treated with base and heat, neutralized, and precipitated as follows. Five $\mu$l each of the rATP and rCTP reactions and 10 $\mu$l each of the rGTP and rUTP reactions were pooled. Two $\mu$l of the pooled reactions were analyzed on a 3% nusieve-1% agarose TBE gel. Two microliters of 0.25M EDTA (pH 8.0) (10 mM final), 10 $\mu$l 1M NaOH (200 mM final), and 10 $\mu$l $H_2O$ were added to the pooled reaction which was then incubated at 98° C. for 10 minutes in a GeneAmp® PCR System 9600 thermal cycler and neutralized with 10 $\mu$l 1M HCl. The pooled reaction was then precipitated by the addition of 150 $\mu$l 95% ethanol followed by an incubation at 4° C. for 15 minutes. It was then microcentrifuged for 15 minutes at 4° C. to collect the precipitate, and the supernatant removed by aspiration. The pellet was washed with 300 $\mu$l 70% ethanol, microcentrifuged for 5 minutes, the supernatant removed by aspiration, and the pellet dried. The pellet was resuspended in 6 $\mu$l formamide:50 mg/ml Blue dextran (in 25 mM EDTA) 5:1 (v/v) and heated at 90° C. for 3 minutes. One and a half $\mu$l of the resuspended pellet was directly loaded onto a pre-electrophoresed 4% acrylamide (29:1 acrylamide:bis, BioRad), 6M urea sequencing gel. It was then electrophoresed and analyzed on a Perkin Elmer ABI Prism™ 377 DNA Sequencer according to the manufacturers instructions. Automated base-calling by the Perkin Elmer ABI Prism™ Sequencing Analysis software resulted in greater than 99% and 98% accuracy for DNA sequence determination of the E678G Tma25 or E678G Tma30, respectively, PCR-amplified 398 base pair products.

We claim:

1. A recombinant thermostable DNA polymerase that is a mutant form of a naturally occurring thermostable DNA polymerase, wherein said naturally occurring thermostable DNA polymerase has an amino acid sequence comprising amino acid sequence motif SerGlnIleGluLeuArgXaa (SEQ ID NO: 2), wherein "Xaa" at position 7 of said sequence motif is a valine residue (Val) or an isoleucine residue (Ile); wherein said mutant form has been modified to contain an amino acid other than glutamic acid (Glu) at position 4 of said sequence motif; and wherein said mutant form possesses reduced discrimination against incorporation of an unconventional nucleotide in comparison to said naturally occurring thermostable DNA polymerase.

2. A nucleic acid sequence encoding a recombinant thermostable DNA polymerase that is a mutant form of a naturally occurring thermostable DNA polymerase, wherein said naturally occurring thermostable DNA polymerase has an amino acid sequence comprising amino acid sequence motif SerGlnIleGluLeuArgXaa (SEQ ID NO: 2), wherein "Xaa" at position 7 of said sequence motif is a valine residue (Val) or an isoleucine residue (Ile); wherein said mutant form has been modified to contain an amino acid other than glutamic acid (Glu) at position 4 of said sequence motif; and wherein said mutant form possesses reduced discrimination against incorporation of an unconventional nucleotide in comparison to said naturally occurring thermostable DNA polymerase.

3. The recombinant thermostable DNA polymerase of claim 1 further characterized in that the ability of said polymerase to incorporate an unconventional nucleotide, relative to the ability of said corresponding native form of polymerase to incorporate said unconventional nucleotide, is increased by at least 20 fold.

4. The recombinant thermostable DNA polymerase of claim 3 further characterized in that said polymerase has sufficient activity for use in a DNA sequencing reaction that comprises an unconventional nucleotide and a corresponding conventional nucleotide in a ratio of 1:1 or less.

5. The recombinant thermostable DNA polymerase of claim 4, wherein said unconventional nucleotide is a ribonucleoside triphosphate.

6. The recombinant thermostable DNA polymerase of claim 5 wherein said ribonucleoside triphosphate is present at a concentration of less than about 100 µM and said corresponding conventional nucleotide is present at a concentration of more than about 100 µM.

7. The recombinant thermostable DNA polymerase of claim 6 wherein said naturally occurring DNA polymerase is selected from the group consisting of *Thermus aquaticus, Thermus caldophilus, Thermus chliarophilus, Thermus filiformis, Thermus flavus, Thermus oshimai, Thermus ruber, Thermus scotoductus, Thermus silvanus, Thermus species Z05, Thermus species sps17, Thermus thermophilus, Thermotoga maritima, Thermotoga neapolitana, Thermosipho africanus, Anaerocellum thermophilum, Bacillus caldotenax,* and *Bacillus stearothermophilus* DNA polymerases.

8. The recombinant thermostable DNA polymerase of claim 6 wherein said naturally occurring DNA polymerase is a thermostable Thermus species DNA polymerase.

9. The recombinant thermostable DNA polymerase of claim 6 wherein said naturally occurring DNA polymerase is a thermostable Thermotoga species DNA polymerase.

10. The recombinant thermostable DNA polymerase of claim 6 wherein said naturally occurring DNA polymerase comprises the amino acid sequence LeuAspTyrSerGlnIleGluLeuArgValLeuAlaHisLeuSer (SEQ ID NO: 5).

11. The nucleic acid sequence of claim 2 wherein said recombinant thermostable DNA polymerase has sufficient activity for use in a DNA sequencing reaction.

12. The nucleic acid sequence of claim 11 wherein said DNA sequencing reaction comprises an unconventional nucleotide and the corresponding conventional nucleotides in a ratio of 1:1 or less.

13. The nucleic acid sequence of claim 12 wherein said unconventional nucleotide is a ribonucleoside triphosphate.

14. The nucleic acid sequence of claim 13 wherein said naturally occurring thermostable DNA polymerase is selected from the group consisting of *Thermus aquaticus, Thermus caldophilus, Thermus chliarophilus, Thermus filiformis, Thermus flavus, Thermus oshimai, Thermus ruber, Thermus scotoductus, Thermus silvanus, Thermus species Z05, Thermus species sps 17, Thermus thermophilus, Thermotoga maritima, Thermotoga neapolitana, Thermosipho africanus, Anaerocellum thermophilum, Bacillus caldotenax,* and *Bacillus stearothermophilus* DNA polymerases.

15. The nucleic acid sequence of claim 13 wherein said naturally occurring thermostable DNA polymerase is a thermostable Thermus species DNA polymerase.

16. The nucleic acid sequence of claim 13 wherein said naturally occurring thermostable DNA polymerase is a thermostable Thermotoga species DNA polymerase.

17. The nucleic acid sequence of claim 12 wherein said naturally occurring DNA polymerase comprises the amino acid sequence LeuAspTyrSerGlnIleGluLeuArgValLeuAlaHisLeuSer (SEQ ID NO: 5).

18. A composition for use in a DNA sequencing reaction that comprises; a nucleic acid template; an oligonucleotide primer complementary to said template; a recombinant thermostable DNA polymerase of claim 5, and a mixture of conventional dNTPs and at least one unconventional nucleotide, wherein said unconventional nucleotide is a ribonucleotide and wherein the ratio of said unconventional nucleotide to said corresponding conventional nucleotide is 1:1 or less.

19. The composition of claim 18 wherein said ribonucleoside is present at a concentration of less than about 100 µM and the corresponding conventional nucleotide is present at a concentration of more than about 100 µM.

20. The composition of claim 19 further characterized in that said unconventional nucleotide is unlabeled.

21. A method for sequencing a nucleic acid target which method comprises the steps of:
   (a) providing an unconventional nucleotide and a corresponding conventional nucleotide in a DNA sequencing reaction, wherein said unconventional and corresponding conventional nucleotides are present in a ratio of less than about 1:1, wherein said DNA sequencing reaction contains a recombinant thermostable DNA polymerase that is a mutant form of a naturally occurring thermostable DNA polymerase, wherein said naturally occurring thermostable DNA polymerase has an amino acid sequence comprising amino acid sequence motif SerGlnIleGluLeuArgXaa (SEQ ID NO: 2), wherein "Xaa" at position 7 of said sequence motif is a valine residue (Val) or an isoleucine residue (Ile); wherein said mutant form has been modified to contain an amino acid other than glutamic acid (Glu) at position 4 of said sequence motif; and wherein said mutant form possesses reduced discrimination against incorporation of an unconventional nucleotide in comparison to said naturally occurring thermostable DNA polymerase;
   (b) treating the reaction of step (a) under conditions for primer extension to provide primer extension products comprising said unconventional nucleotide;
   (c) treating the primer extension products of step (b) under conditions for hydrolyzing said primer extension products;
   (d) resolving reaction products from step (c); and
   (e) determining the sequence of the nucleic acid target.

22. The method for sequencing of claim 21 wherein said unconventional nucleotide is a ribonucleotide.

23. The method for sequencing of claim 22 wherein said ribonucleotide is present at a concentration of about 0.1 µM–100 µM.

24. The method for sequencing of claim 23 wherein said corresponding conventional nucleotide is present at a concentration of about 50 µM–500 µM.

25. A kit for sequencing a nucleic acid comprising a thermostable DNA polymerase enzyme that comprises the amino acid sequence SerGlnIleXaaLeuArgXaa (SEQ ID NO: 1), wherein "Xaa" at position 4 of this sequence is any amino acid residue but not a glutamic acid residue (Glu) and "Xaa" at position 7 of this sequence is a valine residue (Val) or an isoleucine residue (Ile), and a mixture of conventional dNTPs and at least one unconventional nucleotide, wherein the ratio of said unconventional nucleotide to said corresponding conventional nucleotide is less than one.

* * * * *